United States Patent [19]
Hauldren et al.

[11] 4,041,773
[45] Aug. 16, 1977

[54] ULTRASONIC INSPECTION APPARATUS FOR WELL OPERATIONS

[75] Inventors: H. Morris Hauldren, Culloden, W. Va.; Jack R. Claycomb, Lafayette, La.; Deke E. DeKerlegand, Lafayette, La.; Chi-Haung Chang, Lafayette, La.

[73] Assignee: W. C. Lamb, Lafayette, La.

[21] Appl. No.: 620,747

[22] Filed: Oct. 8, 1975

[51] Int. Cl.² ............................................. G01N 29/04
[52] U.S. Cl. ................................................... 73/67.8 S
[58] Field of Search ............... 73/67.8 S, 67.8 R, 67.7, 73/67.5 R, 71.5 US, 151; 324/37 R

[56] References Cited

U.S. PATENT DOCUMENTS

| 2,878,447 | 3/1959 | Price et al. | 324/37 |
|---|---|---|---|
| 3,066,254 | 11/1962 | Price et al. | 324/37 |
| 3,248,933 | 5/1966 | Stebbins | 73/71.5 US |
| 3,540,266 | 11/1970 | Lofgren | 73/67.8 S |
| 3,582,771 | 6/1971 | Placke | 73/71.5 US |
| 3,612,987 | 10/1971 | Placke et al. | 324/37 |

FOREIGN PATENT DOCUMENTS

280,958 9/1970 U.S.S.R. .................... 73/67.8 S

Primary Examiner—Richard C. Queisser
Assistant Examiner—Stephen A. Kreitman
Attorney, Agent, or Firm—Arnold, White & Durkee

[57] ABSTRACT

An ultrasonic inspection apparatus for use in inspecting drill pipe or like tubular members being tripped into and out of a well borehole comprises one or more planarly arranged set of ultrasonic search units, such as wheel search units, arranged on a frame suspendible within the well derrick and defining a vertical passage for the tubular member. Access is provided to the passage by the tubular member from a direction transverse to the longitudinal axis of the tubular member, for example, by providing an openable hinged frame. When in the passage, the pipe is stabilized by wheels exerting a force on the pipe in excess of that exerted by the search units which are biased into sonically coupled contact with the pipe. A linkage on each search unit preserves the angular relation between an electro-acoustical transducer within the search unit and the pipe surface. A method of inspecting tubular goods on the floor of a drilling rig during a tripping operation is also provided.

9 Claims, 10 Drawing Figures

ULTRASONIC INSPECTION APPARATUS FOR WELL OPERATIONS

IDENTIFICATION OF RELATED APPLICATIONS

This application is related in subject matter to copending U.S. Application Ser. No. 620,748, now U.S. Pat. No. 4,020,688, entitled "Ultrasonic Inspection Apparatus for Vertical Members" filed on even date herewith in the name of H. Morris Hauldren, and commonly assigned with this application.

BACKGROUND AND PRIOR ART

This invention relates to a device for the nondestructive ultrasonic testing of tubular goods for detection of small internal cracks and other types of discontinuities or imperfections. More specifically, the device of the instant invention permits on-site inspection of the drill pipe employed in the drilling operation, or well casing or tubing while it is being set, and is particularly useful since it maintains the ultrasonic search units in fixed and constant position relative to the pipe, and enables inspection of the pipe as it is being tripped into the borehole under the rugged conditions prevailing on the rig floor. The novel apparatus permits ready identification of flawed tubular goods which might produce drilling string failures if used when drilling is recommenced.

The use of ultrasonic testing techniques, and specifically of ultrasonic crystals, for detecting discontinuities in metal products is a common mode of nondestructive testing. The crystals employed are typically piezoelectric crystals made of a material such as quartz. These crystals produce ultrasonic vibrations in response to a voltage of appropriate frequency impressed upon the crystal. When inspecting a tubular product for internal flaws using a reflection method, the crystal is maintained in a position relative to the surface of the product to transmit a short duration sonic wave pulse into the product at an angle such that a defect or discontinuity will cause the waves to be reflected to the crystal and produce a voltage response in the crystal. Since the crystal is de-energized immediately following the pulsed emission of a wave, reflected waves are received during de-energized periods, and hence the reflected waves will produce a discernible signal which may be monitored, for example, on a cathode ray tube or a strip chart recorder. Pulse repetition rates between 60 and 2000 pulses per second are employed in various types of inspections.

Typically, an ultrasonic inspection device will be calibrated using a standard identical to the goods being inspected. The standard may have one or more discontinuities of known magnitude so that the response of the device to known imperfections may be ascertained, and standards for accepting or rejecting the inspected goods may be established.

Ultrasonic inspection techniques are most typically employed at the site of manufacture of the articles being inspected. Thus, plate or tubular goods are typically inspected at the manufacturing plant using techniques which are well known in the art. However, the on-site inspection of tubular goods presents different and unique problems.

In well drilling operations, drill pipe failure can be a costly and time-consuming occurrence. Washouts or drill string breakage can occur frequently if drill pipe with sufficiently serious imperfections is employed. Most frequently such failures result from internal flaws in the tubular goods being used. Contrasted with such a failure, it becomes necessary to trip the pipe out of the borehole to replace the failed joint. In the case of drill string breakage, it is also necessary to fish the parted portion of the string from the borehole before drilling can be recommenced. Hence, the value of an efficacious method of inspection, particularly for internal flaws in drill pipe is obvious.

During drilling operations, the drill string is frequently tripped into and out of the borehole to replace a worn drill bit, to set casing at various levels or conduct other operations. During these trips, it is preferred to stack the drill pipe vertically within the well derrick rather than transporting it from the elevated rig floor to racks maintained at ground level. In offshore drilling operations, it is also common to stack drill pipe vertically. Inspection of a drilling string is desirably conducted periodically, e.g., every two or three months, to detect the existence of flaws on drill pipe which would render the pipe susceptible to failure in subsequent drilling operations. Hence to provide most efficient inspection of tubular goods in well drilling operations, it is necessary to provide an inspection device which can inspect tubular goods in a vertical position in the well derrick. With such a device inspections could be conducted during a tripping operation made necessary by factors such as a replacement of a worn drill bit. Furthermore, since it is necessary to join individual stands of pipe (comprising typically two or three pipe joints or sections) at the rig floor level when assembling a drilling string, it is necessary that a useful inspection device be readily engaged and disengaged from about the pipe being inspected.

The sensitivity of ultrasonic inspections, however, can be adversely affected by the severe conditions prevalent on a drilling rig. A suspended pipe can move laterally or can be vibrating as a result of the insertion or withdrawal operation. Such conditions make it difficult to maintain adequate sonic coupling between the search unit and the pipe. However, such movement can alter the angles at which the sonic emissions enter the wall of the member being inspected. It is accordingly necessary to provide a rugged device to conduct such on-site inspection to obtain the most accurate and dependable readouts.

SUMMARY OF THE INVENTION

In accordance with the instant invention, there is provided a device for nondestructive ultrasonic inspection of tubular goods disposed in a substantially vertical position. Specifically, the instant invention provides an ultrasonic inspection apparatus which is readily movable into and out of engagement with the member being inspected while maintaining a plurality of ultrasonic search units in stable position relative to the tubular member. Accordingly, the device of this invention may be advantageously employed for inspection of tubular goods used on well operations at a well derrick while tubular members are being tripped into or out of a well borehole. In a particular embodiment, this invention provides a device for simultaneously conducting multiple inspections for discontinuities transverse to and parallel to the axis of the tubular member, and also conduct measurements of wall thickness.

The instant invention also provides a novel method of inspecting tubular goods while they are being tripped into or out of a well borehole.

When a pipe is being tripped out of a borehole, the surface of the pipe is typically covered with drilling mud and drilling debris. Also, there may exist liquid films flowing on the interior of the pipe as the pipe is withdrawn from a liquid-filled borehole. The existence of drilling mud or debris on the exterior of the pipe can create coupling difficulties with an ultrasonic inspection device. Moreover, liquid films flowing down a pipe can create false "reflections" which would mask the existence of discontinuities or flaws which are sought to be detected. Accordingly, unless a drill pipe can be substantially cleaned during its withdrawal from the borehole, the device of the instant invention will be more typically employed to conduct the ultrasonic inspection during a pipe tripping operation into the borehole.

In copending application Ser. No. 620,748, identified more fully above, there is disclosed an apparatus for ultrasonic inspection of vertical members, such as pipe suspended in a well derrick. In accordance with a first aspect of the invention there is provided an ultrasonic inspection device wherein a plurality of ultrasonic search units mounted on a frame are maintained sonically coupled to the tubular member, and the unit is positively stabilized with respect to the tubular member while permitting relative movement of the tubular member through the inspection device. In addition, the search units which include electro-acoustic transducers which are disposed at a precise angle relative to the tubular member being inspected are mounted on the frame utilizing a linkage which maintains the angular relation between the transducer and the tubular member constant, and hence provides accurate inspection information. The linkage also minimizes adjustments which must be made in the device when pipe of different diameter is inspected.

The inspection apparatus of the invention includes a frame having a plurality of ultrasonic search units thereon, which frame may be disposed around a tubular member in the vertical position. The frame has a central vertical passage around which the search units are disposed. The passage is accessible from a direction transverse to the axis of the tubular member. For example, the frame may be hinged so that is may be opened to accept the tubular member. Once in the vertical passage the tubular member is stablized within the device by means of a plurality of guides or stablizers mounted on the frame. The stablizers are independently mounted from the search units on the frame and are pressed against the tubular member with a force greater than any forces maintaining the search units in sonically coupled relation with the tubular member. Hence any movement of the tubular member is absorbed by the stablizers which then maintain the frame in position to preserve the sonic coupling of the search units through the movement.

In accordance with a further embodiment of this invention, there is provided apparatus for simultaneously conducting a plurality of different inspections on a tubular member used during well operations. An inspection of primary interest involves ultrasonic monitoring of a tubular member for discontinuities transverse to the longitudinal axis of the member. Such an inspection is conducted by sonically coupling a plurality of ultrasonic search units around the member to be inspected to provide a combined beam spread which covers the entire circumference of the member. In such an operation, the search units are disposed to transmit ultrasonic pulses into the wall of the tubular member at an angle acute to the longitudinal axis of the member being inspected and in a direction coextending with the longitudinal axis, as generally described in copending Application Ser. No. 620,748.

However, such an ultrasonic inspection generally is not indicative of the existence of discontinuities parallel to the longitudinal axis of the tubular member. In addition, wall thickness of a tubular member is another parameter which is of interest in determining the potential failure characteristics of tubular goods used in drilling operations.

Accordingly, this invention includes a novel inspection device capable of performing, during the same tripping operation, a plurality of inspection functions including searching for discontinuities transverse to and generally parallel to the longitudinal axis of a pipe and monitoring the thickness of a single wall. The inspection device in accordance with this invention includes a multi-tiered inspection buggy having a generally vertical passage accessible by the tubular member from a direction transverse to its longitudinal axis. Each tier of the buggy includes search units sonically coupled to the pipe and disposed to conduct one of the desired search operations, i.e., search for transverse discontinuities, parallel discontinuities and monitor wall thickness. A plurality of stablizers sufficient to maintain the tubular member in stable position relative to the buggy are provided; however, it is not necessary that stablizers be included on each inspection tier. Preferably each of the search units on each tier are independently mounted to maintain a constant angle between the electro-acoustical transducers within the search unit and the tubular member being inspected.

In accordance with the novel method of this invention, tubular members suspended in a well derrick may be inspected with improved efficiency by sonically coupling a plurality of ultrasonic search units containing electro-acoustical transducers to the member, maintaining the pipe in stable position relative to the search units by guiding the pipe with a force greater than that exerted on the pipe by the search units, and maintaining a constant angle between each of said electro-acoustical transducers and the pipe during the inspection. In further accordance with the invention there is provided a method for conducting multiple inspections of vertically disposed tubular members used in well operations which comprises sonically coupling search units to the pipe in separate coplanar positions for each inspection operation to be conducted. The search units adapted for inspecting for discontinuities transverse to the longitudinal axis are disposed in uppermost or lowermost position to produce a sonic beam within the tubular member directed away from the plane or planes in which other inspection operations are conducted. Preferably, the search units adapted to inspect for discontinuities transverse to the longitudinal axes of the tubular member are uppermost on the multi-tiered inspection buggy and are directed to scan upwardly along the pipe as it is moved into or out of the borehole.

BRIEF DESCRIPTION OF THE DRAWINGS

This invention will further be illustrated by reference to the appended drawings which illustrate particular embodiments to the ultrasonic inspection device in accordance with this invention.

DESCRIPTION OF THE SPECIFIC AND PREFERRED EMBODIMENTS

Figure 1:
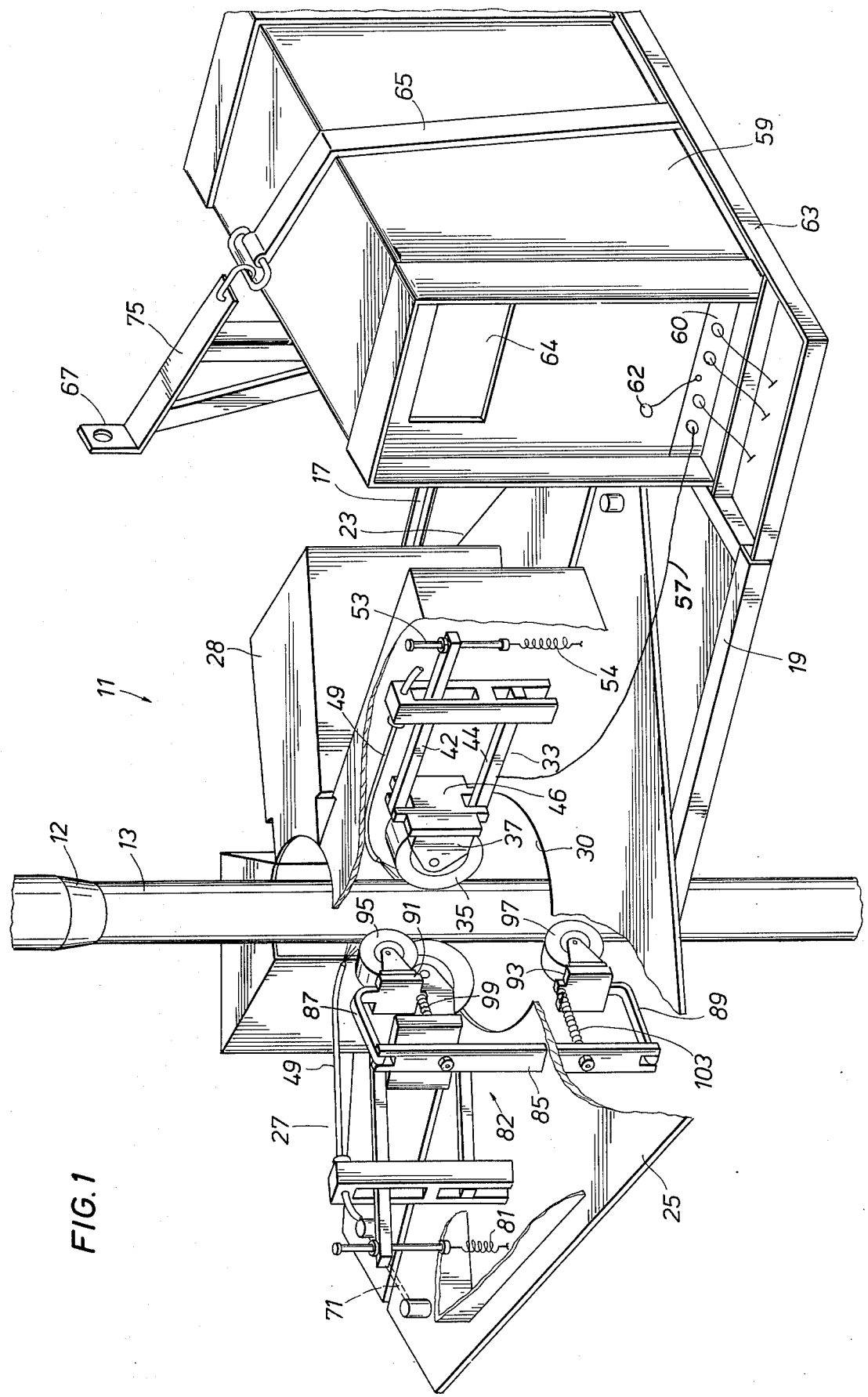
FIG. 1 is a perspective view of an ultrasonic inspection apparatus in accordance with this invention shown in place on a drill pipe and disposed over the rotary table on a drilling platform.

Referring now to FIG. 1, there is shown in perspective view an ultrasonic inspection apparatus 11 in accordance with this invention in position around a pipe section 13 disposed through the rotary table opening on a drilling rig floor 15. Pipe 13 is joined at joint 12 with other section of pipe and is suspended in a well derrick (not shown) by means of an elevator or like device (not shown). The ultrasonic inspection device comprises a frame having two generally parallel horizontally disposed members 17 and 19 spanned by brace 21. Two base plates, 23 and 25, are pinned for pivotal movement parallel to the frame at points 24 and 26, respectively. Latch 71 at the opposite end of plates 23 and 25 served to hold the plates in closed position around the pipe 13. An opening in base plates 23 and 25 in the center portion thereof defines a central vertical passage 30 in the apparatus. A shroud 28 having a corresponding central passage and four separate compartments encloses the ultrasonic inspection apparatus 11.

Each base plate supports two transducer search units and two transducer mounting linkages. Specifically, base plate 23 supports transducer mounting linkages 29 and 31 (not in view in FIG. 1), while base plate 25 supports transducer mounting linkages 27 and 33. Each of the transducer mounting linkages is identical in construction, and hence the description shall be in reference to transducer mounting linkage 33.

It will be understood that in accordance with this invention, any desired number of ultrasonic search units may be used to effect the pipe inspection. The illustrated embodiment shows four such search units arranged around the pipe on 90° centers. However, it may be satisfactory depending upon the size of the pipe, the particular inspection operation, and the beam spread of the ultrasonic transducers employed to utilize more or less ultrasonic search units. When scanning the pipe for imperfections or discontinuities transverse to the axis of the tubular member being inspected, it is sufficient so long as the beam spread units permits a survey of the entire circumference of the pipe as it passes through the apparatus. Three or four units are most often used for the transverse discontinuity inspection.

For longitudinal discontinuity inspection, the electroacoustic transducers are arranged in a plane parallel to the axis of the pipe to transmit a beam which travels around the pipe in a section generally perpendicular to the longitudinal axes. As few as two and up to four coplanar search units are used for this operation depending primarily on the diameter of the member being inspected.

Thickness measurement is effected by a sonic beam transmitted perpendicular to the surface of the pipe. This beam measures thickness only beneath the search units. Hence up to four or even more units may be employed depending upon how closely thickness is to be monitored. On a large diameter pipe, a complete thickness inspection could require more than four units. Often it may be sufficient, on the other hand, to use two search units to monitor thickness, cognizant that these units will give only a general indication of pipe condition, and are not likely to pick up all areas of wear or corrosion.

Figure 1A:
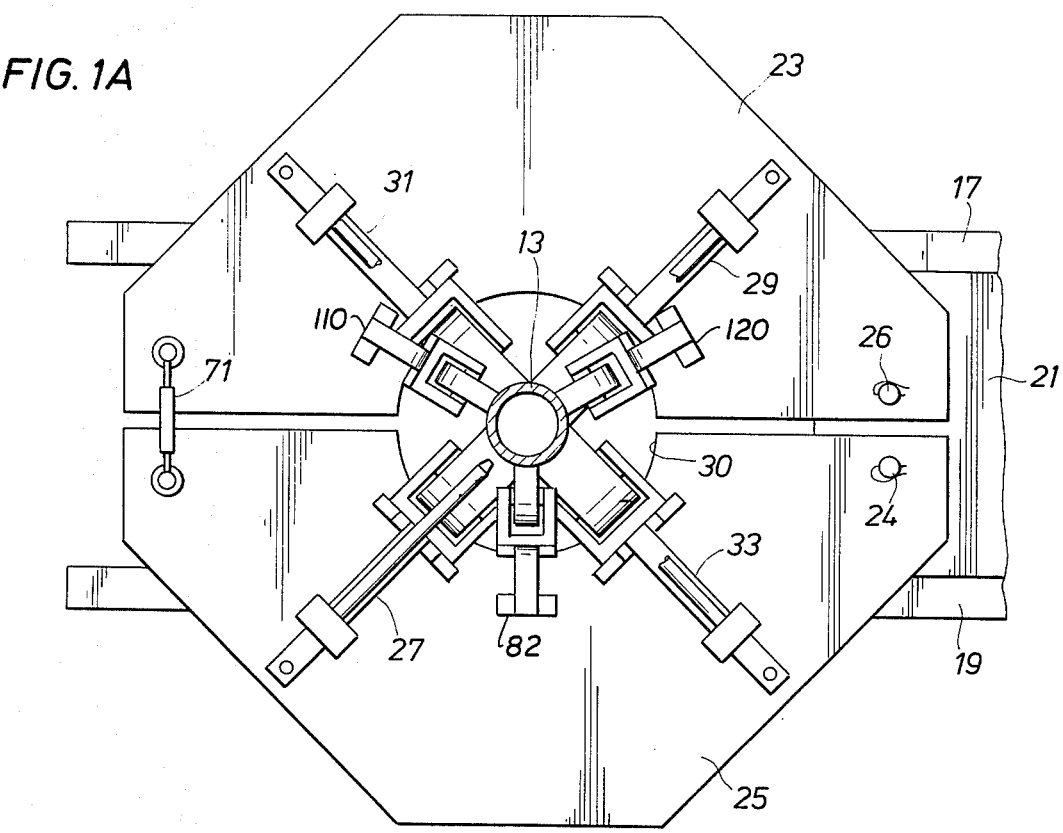
FIG. 1A is a top view of the ultrasonic inspection apparatus illustrated in FIG. 1.

Referring next to FIG. 1A, there is illustrated a top view of the ultrasonic inspection apparatus 11 in full view with shroud 28 removed. Search units 27, 29, 31 and 33 are equally spaced around pipe 13 under inspection to fully irradiate its circumference. Mounted between the search units are stabilizers 82, 110 and 120 which apply an inwardly directed force to pipe 13 to restrain swaying motion in pipe 13 during tripping. The force exerted by the stabilizers, as will be appreciated, is of a magnitude greater than that exerted on the pipe by the search units.

The frame comprising parallel members 17 and 19 and support plate 21 is open at the end opposite the plate 21. The open end permits the inspection apparatus to re-moved from pipe 13 quickly and easily after base plates 23 and 25 have been unlatched and pivoted outwardly. Preferably, in order to scan for discontinuities transferse to the longitudinal axis of a tubular member, the search unit should have its piezoelectric crystal disposed at an angle approximately 45° to the axis of the tubular member being inspected. This angle may vary slightly depending upon the size and wall thickness of the pipe being inspected. For example, on some pipe having a diameter between 3½ and 4½ inches, it has been found that an attack angle of the sonic beam from the piezoelectric cyrstal is optimal at an angle of 43½ to the longitudinal axis of the pipe when inspecting for transverse discontinuities. However, in determining the optimal disposition of the piezoelectric crystal, it is preferred to initially calibrate the unit with a standard test pipe section having a discontinuity of known dimension. The unit is activated and the angle of attach of the piezoelectric crystal is adjusted until the known discontinuity gives the maximum electrical response. Available search units have the capability of adjusting to the member being inspected and use of such variable angle beam search units is preferred.

It is desirable to be able to set up the inspection apparatus with the optimum beam angle and utilize the apparatus to inspect tubular members of various diameters without making correction adjustments to reset the beam angle. Mounting linkage 33 provides this desirable feature.

Figure 2:
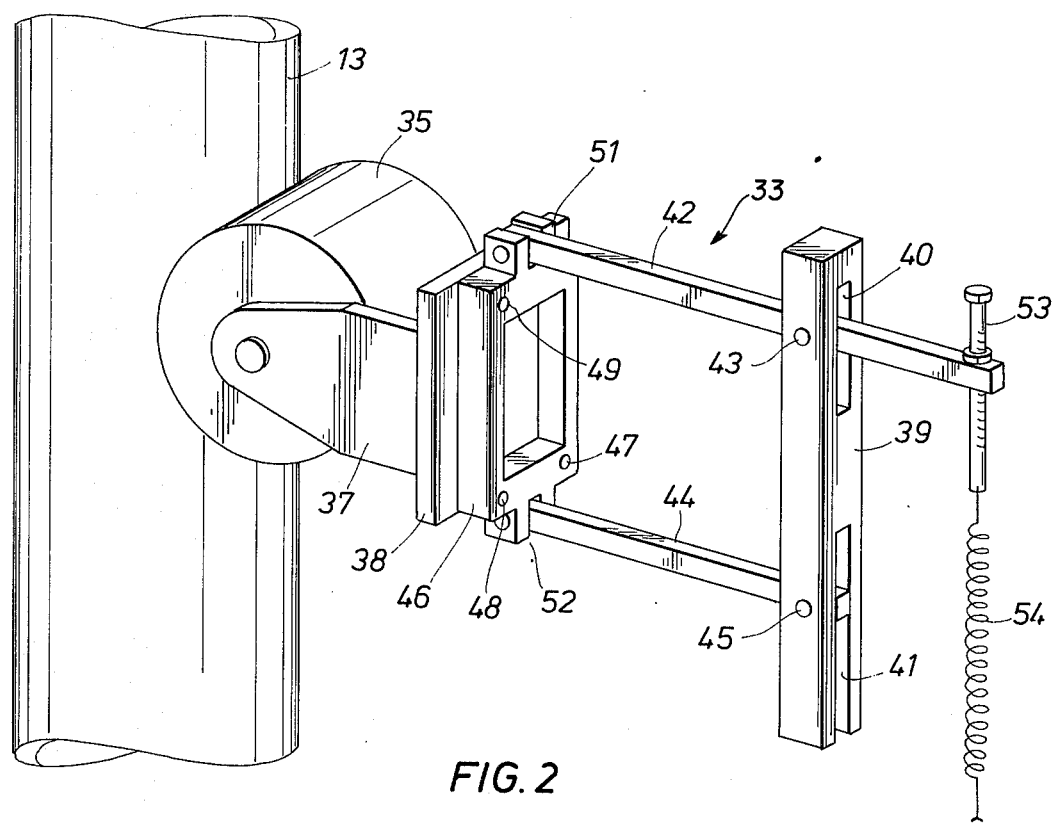
FIG. 2 is a perspective view of an ultrasonic search unit device employed in the inspection apparatus of FIG. 1, specifically showing a mounting linkage urging a rolling wheel into contact with a pipe being inspected.

Referring now to FIG. 2, there is shown in perspective mounting linkage 33 positioning a search unit proximate pipe 13. Mounting linkage 33 comprises a vertically standing member 39 having a rectangular-shaped opening 40 formed at the upper end and a slot 41 at the lower end. Vertical member 39 is securely attached to base plate 25 to rigidly hold the search unit in position. An upper arm 42 extends through the opening 40 and is held therein by a pin providing upper arm 42 with pivotal movement in the vertical plane. A shorter lower arm 44 is disposed in slot 41 and provided with pivotal movement in the vertical plane about a pin 45. A rectangular adapter plate 46 is designed to mate with base plate 38 of the wheel search unit to mount the same with, for example, counter-sunk screws 47, 48, 49 and 50 (not shown). A clevis 51 is formed on the top edge of the adapter plate 46 with a similar clevis 52 formed on the bottom edge of plate 46. Clevis 51 and clevis 52 pivotally receive upper arm 42 and lower arm 44, respectively, to pivotally support adapter plate 46.

The rearwardly extending portion of upper arm 42 is threaded and receives a bolt 53. A spring 54 or other biasing means attaches to the lower end of bolt 53 and also attaches to the base plate 25. Bolt 53 permits the spring tension and consequently the force on arm 42 to be adjusted to a desired magnitude.

It will be apparent that the mounting linkage 33 provides the wheel search unit with inward movement toward the central passage 30, yet maintains the base plate 38 of the search unit parallel with the tubular member 13. Therefore, the beam angle from the piezoelectric crystal can be set to the optimum value and so maintained regardless of the size of tubular member that is being inspected.

Figure 3:
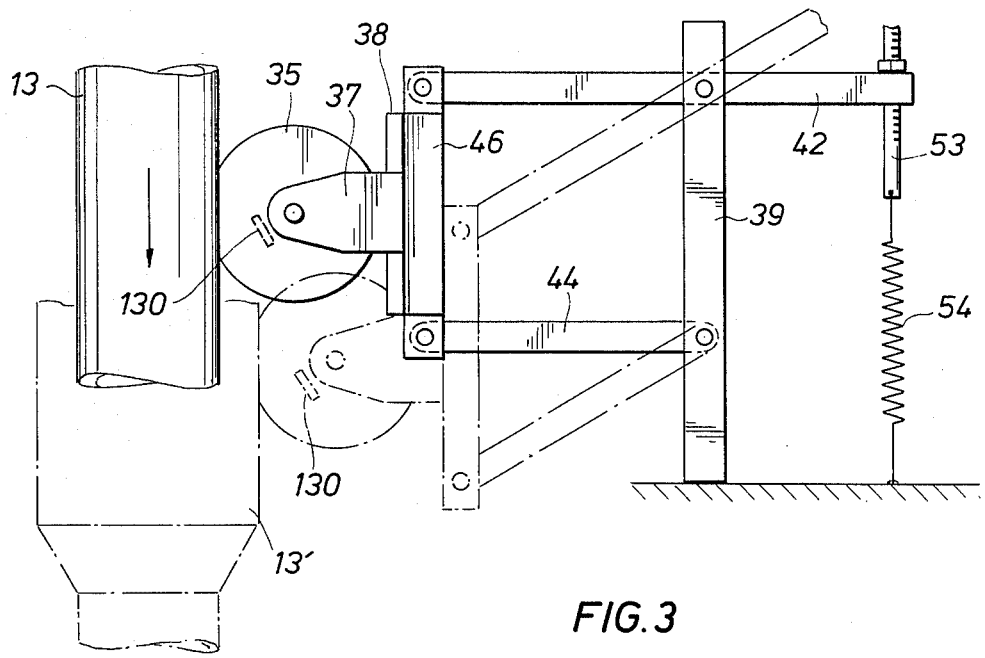
FIG. 3 is a side schematic view of the ultrasonic transducer device and mounting linkage of FIG. 2.

With reference to FIG. 3, a side schematic illustration of the rolling wheel search unit and mounting linkage of FIG. 2, the operation and advantages of the instant mounting linkage can be more fully appreciated.

With the smaller diameter pipe 13, the mounting linkage 33 has the upper arm 42 and the lower arm 44 in a substantially horizontal position. The transducer 130 carried within the wheel 35 is at the optimum beam angle with respect to pipe 13.

When a larger diameter pipe is being inspected, arms 42 and 44 move to a downwardly inclining position. Because adapter plate 46 is pivoted to the ends of arms 42 and 44, thereby forming a parallelogram like structure, adapter plate 46 moves downwardly and maintains its upright attitude. With adapter plate 46 remaining unchanged in its attitude, the transducer 130 also remains in its prior orientation and consequently the beam angle does not change.

The search unit employed in the device of this invention is preferably a variable angle beam wheel search unit of a type well known in the art. Such wheel search units are manufactured, by Sperry Division of Automation Industries, Inc. The wheel search unit is typically comprised of a flexible tirelike wheel 35 mounted for rotation about an axis supported by bracket 37. The piezoelectric crystal is mounted on a non-rotating axle within the wheel. The flexible tire 35 is then filled with a suitable coupling agent. Coupling agents which have been used in the art include glycols or glycol ethers, for example, the Cellusolve products sold by Union Carbide Corporation.

Figure 4:
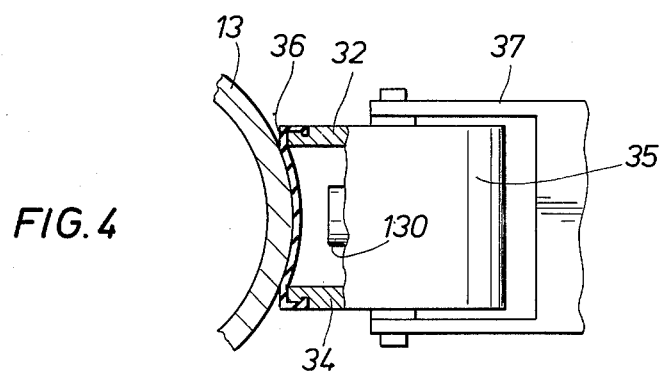
FIG. 4 is a partially sectioned plan view of the ultrasonic transducer device of FIGS. 2 and 3.

Wheel 35 is shown in partial section in FIG. 4, with the flexible outer covering 36 pressed firmly against pipe 13. Flexible outer covering 36 is securely attached to side supports 32 and 34 of wheel 35, and when pressed against pipe 13, the outer covering conforms to the curvature of the outside pipe surface. Side supports 32 and 34 prevent wheel covering 36 from blowing out by limiting the extent to which the flexible covering 36 can be deformed. A search unit of this type is that disclosed in U.S. Pat. No. 3,628,375, issued to Dominick A. Pagano.

Wheel 35 is pressed against pipe 13 to maintain adequate pressure contact therewith by the force applied to it from spring 54 of linkage 33, as it acts through upper arm 42. The force applied can, however, be changed by adjusting the length of bolt 53 extending through upper arm 42.

In order to accomplish coupling between the flexible tire 35 and the tubular member 13 being inspected, it is preferred to provide a liquid coupling agent on the surface of the pipe. Accordingly, water lines such as 49 (FIG. 1) are provided above each wheel search unit to inject a constant stream of water to create a uniform film between flexible tire 35 and the pipe being inspected to serve as a sonic coupling agent. Tubes 49 are fed through manifold 72 which receives water through a water transport line 73 that is connected to a suitable water supply (now shown) through valve 61. A gravity flow of water is satisfactory to provide a coupling agent to the search units, although a pumped source may also be employed. It will be understood by those skilled in the art that other coupling agents may be used rather than water during operation of the device. However, water operates satisfactorily and is clearly the most available and least expensive coupling agent to be used on the exterior of the pipe being inspected.

Referring again to FIG. 1, also mounted on base plates 23 and 25 and normally enclosed by shroud 28 are stabilizers of which only stabilizer 82 is in view. The stabilizers serve to apply a radially, inwardly directed force at several locations around tubular member 13 to minimize swaying motion of tubular member 13 as it is being moved through the inspection device for inspection.

Stabilizer 82 comprises a support 85 extending above and below base plate 25 parallel to the centerline of the central passage 30. At each end of support 85, there is attached a pivot arm 87, 89 which carries a mount 91, 93 to which stabilizer wheels 95, 97 are affixed. A spring 99 connects between mount 91 and support 85 to urge wheel 95 against tubular member 13, and similarly, a spring 103 connects between mount 93 and support 85 to urge wheel 97 against tubular member 13, thereby together applying a restraining force to the tubular member 13.

Although there are three stabilizers employed in the preferred embodiment (see FIG. 1A), additional stabilizers could be utilized. The maximum number will, of course, be dependent upon the size of pipe being inspected. Also, it is preferable to have the upper and lower pipe contacting portions of the stabilizers spaced away from and located in a plane different from the search units.

Figure 5:
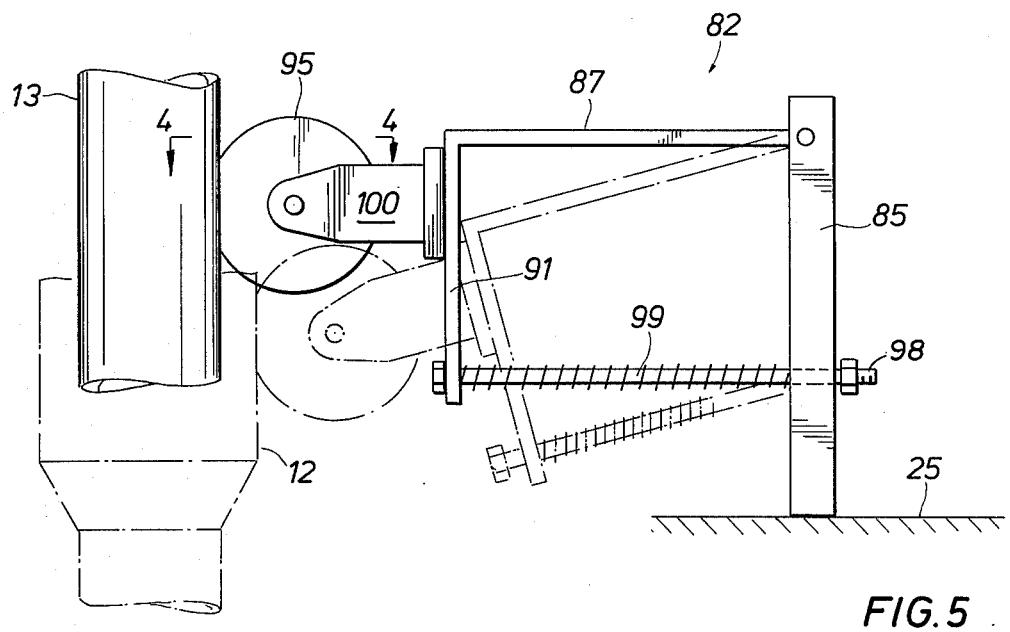
FIG. 5 is a side schematic view of a stablizer employed in the inspection apparatus of FIG. 1.

The upper portion of stabilizer 82 extending through and firmly held in base plate 25 is illustrated in schematic in FIG. 5. Specifically, FIG. 5 illustrates the operation of stabilizer 82 and its ability to function with various pipe diameters and permit passage of pipe joints. As shown, the structure formed of pivot arm 87 and mount 91 is pivoted about the upper end of vertical support 85. A bolt 98 extends from the lower portion of mount 91 and through support 85 with spring 99 carried thereon and held in compression. Stabilizer wheel 95 is attached to mount 91 through a bracket 100 and is urged into contact with pipe 13 by spring 99.

When it is desired to inspect a larger diameter pipe, pivot arm 87 and wheel 95 pivot about the upper end of support 85, moving inwardly and slightly downwardly. Spring 99 compresses further, maintaining an adequate radially inwardly directed force on the pipe. Also, as indicated in dotted outline in FIG. 5, the stabilizers easily permit passage of pipe joints while maintaining stabilization of the pipe 13.

Opposite the search units on the support frame, there extends platform 63 of suitable size and dimension to support an ultrasonic inspection instrument 59. Ultrasonic inspection instrument 59 includes a pulse generator and receiver unit as well as an oscilloscope. Such ultrasonic search instrument are well known in the art. For example, Sperry Division of Automation Industries offers a 10M pulser receiver unit packaged with a type UM, style 50E533 oscilloscope which may be used with the inspection device in accordance with the invention. Also, smaller battery operated search instruments are available and can be used satisfactorily.

The pulser within instrument transmits a series of pulses which are simultaneously transmitted to the piezoelectric crystals in the wheel search units through transmission line 57 shown existing junction block 60. Typically available search units provide only a single pulse output. Junction block 60 merely divides the signal to the four transmission lines and hence optimally turning the signal transmission path to each wheel search unit. Impedance matching techniques being well known in the art, the details will be omitted. During periods when the piezoelectric crystals are de-energized, reflected signals from discontinuities within the tubular member are sensed and are transmitted through the transmission lines 57 to junction block 60 which provides a single output signal at jack 62 of the pulser/receiver portion of instrument. The signal is amplified in the pulser/receiver portion of instrument 59 and displayed on oscilloscope 64; although it is pointed out that a strip chart recorder may be used in place of or in addition to the CRT display.

The pulsing frequency employed in connection with inspection operations using the apparatus of this invention may vary as will be understood by those skilled in the art. Typical inspection operations may be conducted at frequencies of 1 megacycle to 5 megacycles. Eminently successful inspections have been conducted utilizing a frequency of 2.25 megacycles.

The arrangement of the inspection search units, the junction block, the pulser/receiver and the CRT display or strip chart recorder display is best understood from the schematic illustration of FIG. 5 of the referenced, copending application Ser. No. 620,748.

Instrument 59 is retained on platform 63 by means of a strap 65 which is engaged at its upper end by a hook extending from support 75. Support 75 terminates in an eye 67 or other connecting device, which may be engaged to an overload line 77 on the well derrick. Eye 67 is desirably provided over the center of gravity of the entire apparatus so that during use, minimal lateral forces are imposed upon the search units engaging the tubular member being inspected.

Accordingly, when the apparatus in accordance with this invention is to be used, latch 71 (FIG. 1) is released and plates 23 and 25 are pivoted outwardly to enable the pipe 13 to be received between support 17 and 19. The device is manually manipulated until pipe 13 is disposed centrally between the supports and plates 23 and 25 are swung back to their original positions and latched in place with latch 71. Springs 81 will then urge each wheel search unit into engagement with the tubular member and the passage of the pipe into the borehole commences. When the tubular members encounter joint 12, the biasing springs will yield permitting the search units to ride over the pipe joint. If a discontinuity is detected, latch 71 is loosed and the search unit is manually removed from pipe 13. The faulty joint may then be replaced and after the string is reconnected, the inspection apparatus is repositioned around the pipe to continue the inspection operation.

Figure 6:
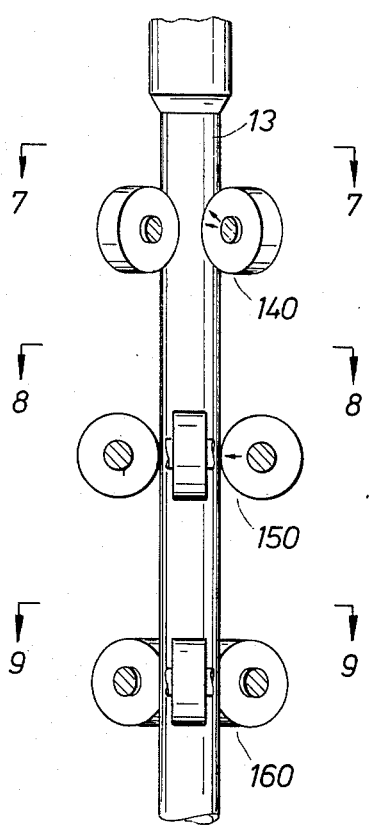
FIG. 6 is a schematic of a multi-tiered inspection apparatus in accordance with the present invention.

With reference now to FIG. 6, there is illustrated in a simple schematic drawing, a three tier ultrasonic pipe inspection apparatus for inspecting to detect the presence of discontinuities transverse to the longitudinal axis of the pipe and discontinuities running substantially longitudinally through the pipe, and to inspect for wall thickness. The wheel search units in a multi-tier inspection apparatus would be mounted in exactly the same fashion as are the wheel search units of the embodiment of FIG. 1. Specifically, a parallelogram-like linkage (similar to linkage 33 of FIG. 3) would utilized for each wheel search unit. Each group of search units 140, 150 and 160 would be mounted on a pair of base plates (similar to base plates 23 and 25 of FIG. 1) with the three pairs of base plates being connected together by vertical stanchious. Therefore, when necessary to remove the three tier apparatus from around a pipe string, a holding latch is released permitting the three tier base plate structure to separate into two pivoted halves.

Although the specific arrangement of the wheel search unit groups 140, 150 and 160 could be varied, the transverse discontinuity detecting group 140 is shown mounted as the top tier with the transducer directing sonic waves upwardly into the pipe 13 as shown by the arrows. The central group 150 of wheel search units detects wall thickness; and as indicated by the arrows, the transducers direct sonic waves radially inward. The lower group of search units 160 detects longitudinal discontinuities in pipe 13. The transducers in that group direct sonic waves laterally into the pipe 13. It is pointed out, however, that the upper group 140 and the lower group 160 can be reversed, as the only requirement is that sonic waves from the various groups must not create interference.

Figure 7:
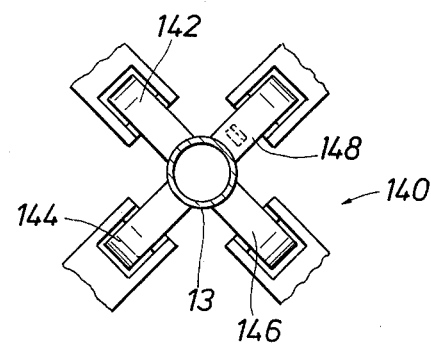
FIG. 7 is a plan view of the upper tier of the multi-tiered inspection apparatus illustrated in FIG. 6 along line 7—7.
Figure 8:
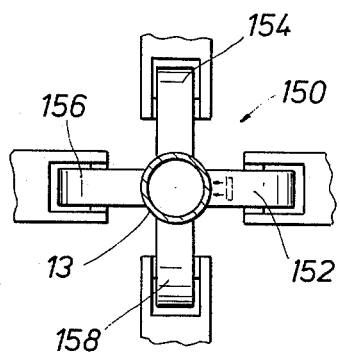
FIG. 8 is a plan view of the middle group of search units employed in the apparatus of FIG. 6 along line 8—8.
Figure 9:
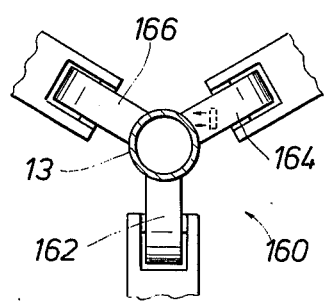
FIG. 9 is a plan view of the lower tier of search units employed in the apparatus of FIG. 6 along line 9—9.

Referring now to FIGS. 7, 8 and 9, there are illustrated separate plan views of each tier of search units. FIG. 7 shows the search units 142, 144, 146 and 148 as being equally spaced about the circumference of the pipe 13. Also, in FIG. 7, the transducer of search unit 148 is shown disposed at a slightly upward aiming angle. FIG. 8 similarly shows the search units 152, 154, 156 and 158 as being equally spaced about the pipe 13. The transducer of search unit 152 is shown directing sonic waves directly into pipe 13 without lateral offset. FIG. 9 shows the three search units 162, 164 and 166 of group 160 with the transducer of search unit 164 directing sonic waves laterally into pipe 13.

From the plain views of FIGS. 7-9, it is observable that the search units in the three groups will each roll along a separate and distinct path. However, an equally effective inspection apparatus could have the search units of the groups aligned to roll along common pathes.

Each group of search units can be provided with a separate visual display device such as, for example, an ultrasonic search instrument comprising a pulser/receiver and CRT oscilloscope.

The foregoing description of the invention has been directed to a particular preferred embodiment for purposes of explanation and illustration. It will be apparent, however, to those skilled in this art that many modifications and changes in both apparatus and method may be made without departing from the scope and spirit of the invention. For example, the frame which is supported from overhead by a hook and cable could instead be supported by a carriage adapted to move on the rig floor into position approximate the drilling table. Also, with appropriate modifications to the extension platform attached to the frame and modification to the junction block, separate visual display of each wheel search unit could be provided. These, and other modifications of the invention will be apparent to those skilled in this art. It is the applicants' intention in the following claims to cover all such equivalent modifications and variations as fall within the true spirit and scope of the invention.

What is claimed is:

1. Apparatus for ultrasonic inspection of vertical tubular members which comprises:
   a frame defining a vertical passage for said tubular member accessible from a direction transverse to the longitudinal axis of said tubular members;
   a plurality of ultrasonic search units disposed on said frame, each including an electro-acoustical transducer for transmitting an ultrasonic signal into the wall of said member;
   a mechanism mounted each search unit on said frame to yieldably urge said ultrasonic search unit into contact and sonically coupled relation with the surface of the tubular member;
   said mechanism providing each search unit with self-adjusting radial movement relative to said vertical tubular member, enabling the unit to adapt to changes in the size of said tubular member inspected without altering the orientation of the transducer inside said search unit with respect to the surface of said tubular member.

2. The apparatus of claim 1 wherein said search units are wheel search units arranged to roll on the outer surface of the tubular member along a path parallel to the longitudinal axis of the member.

3. The apparatus of claim 1 including stabilizer means for engaging said tubular member to maintain said frame in a stable position realtive to said member, said stabilizer means engaging the tubular member in at least two positions longitudinally spaced along the axis of the tubular member.

4. The apparatus of claim 3 wherein said stabilizer means comprises at least two sets of coplanarly arranged wheels adapted to engage the surface of said tubular member.

5. The apparatus of claim 1 wherein said frame defines at least two longitudinally spaced horizontal mounting planes for said search units, and wherein the search units on each mounting plane are arranged to perform different inspection operations.

6. The apparatus of claim 5 wherein the search units in at least one of said planes are arranged to transmit a signal longitudinally within the wall of said tubular member a direction away from the remaining of said planes to inspect for discontinuities transverse to the longitudinal axis of the member.

7. The apparatus of claim 6 wherein said frame defines three mounting planes and wherein the search units on the uppermost frame are arranged to inspect for discontinuities transverse to the longitudinal axis of the tubular member.

8. Apparatus for ultrasonic inspection of vertical tubular members which comprises:
   a frame defining a vertical passage for said tubular member accessible from a direction transverse to the longitudinal axis of said tubular members;
   a plurality of ultrasonic search units disposed on said frame, each including an electro-acoustical transducer for transmitting an ultrasonic signal into the wall of said member;
   a linkage mounting each search unit on said frame for yieldably urging said ultrasonic search units into contact and sonically coupled relation with the surface of the tubular member and maintaining a constant angle between said transducer and the surface of said member;
   said linkage comprising a hinged parallelogram linkage on each search unit having one side affixed relative to said frame and the opposing side affixed to said search unit; and
   stabilizer means for engaging said tubular member with a force in excess of that composed between the tubular member in said search units to maintaining said frame in stable relation relative to said member upon relative horizontal movement between said frame and the tubular member.

9. A method of inspecting a tubular member used in well drilling operations on a drilling platform of a well derrick while said member is being inserted in or retrieved from a well borehole which comprises:
   vertically suspending said tubular member within the well derrick;
   sonically coupling around the periphery of the tubular member a plurality of ultrasonic search units each containing an electro-acoustical transducer disposed in a specific angular relation to the surface of the tubular member to the suspended tubular member;
   moving said tubular member vertically relative to said borehole while radially self-adjusting said search units relative to said vertical member to adapt to changes in the size of said tubular member, yet maintain the transducers within said search units in fixed angular position relative to the surface of the tubular member.

* * * * *